(12) United States Patent
Tournoud et al.

(10) Patent No.: US 11,414,692 B2
(45) Date of Patent: Aug. 16, 2022

(54) METHOD AND DEVICE FOR CHARACTERIZING THE INHIBITORY CAPACITY OF A MOLECULE ON A MICROORGANISM

(71) Applicant: BIOMERIEUX, Marcy l'Etoile (FR)

(72) Inventors: Maud Tournoud, Grenoble (FR); Pierre Mahe, Lans en Vercors (FR)

(73) Assignee: BIOMERIEUX, Marcy l'Etoile (FR)

( * ) Notice: Subject to any disclaimer, the term of this patent is extended or adjusted under 35 U.S.C. 154(b) by 1264 days.

(21) Appl. No.: 15/536,473

(22) PCT Filed: Nov. 30, 2015

(86) PCT No.: PCT/FR2015/053258
§ 371 (c)(1),
(2) Date: Jun. 15, 2017

(87) PCT Pub. No.: WO2016/097518
PCT Pub. Date: Jun. 23, 2016

(65) Prior Publication Data
US 2017/0349932 A1 Dec. 7, 2017

(30) Foreign Application Priority Data
Dec. 15, 2014 (FR) ........................ 1462408

(51) Int. Cl.
| | |
|---|---|
| *C12Q 1/18* | (2006.01) |
| *C12Q 1/06* | (2006.01) |
| *G01N 33/569* | (2006.01) |
| *C12Q 1/04* | (2006.01) |
| *G16B 99/00* | (2019.01) |

(52) U.S. Cl.
CPC ............... *C12Q 1/18* (2013.01); *C12Q 1/04* (2013.01); *C12Q 1/06* (2013.01); *G01N 33/569* (2013.01); *G16B 99/00* (2019.02)

(58) Field of Classification Search
None
See application file for complete search history.

(56) References Cited

U.S. PATENT DOCUMENTS

2012/0077206 A1   3/2012   Metzger et al.

FOREIGN PATENT DOCUMENTS

| EP | 0010846 A1 | 5/1980 |
|---|---|---|
| FR | 2916761 A1 | 12/2008 |
| WO | 2005/021559 A2 | 3/2005 |
| WO | 2008/078911 A1 | 7/2008 |
| WO | 2008/107881 A2 | 9/2008 |
| WO | 2012/073202 A1 | 6/2012 |
| WO | 2014/155020 A1 | 10/2014 |

OTHER PUBLICATIONS

Baranyi et al. (Applied and Environmental Microbiology Feb. 1999:732-736).*
Baraban et al., "Millifluidic droplet analyser for microbiology," Lab Chip, 2011, pp. 4057-4062.
Kahm et al., "grofit: Fitting Biological Growth Curves with R," Journal of Statistical Software, vol. 33, Issue 7, Feb. 2010, 21 pages.
Feb. 3, 2016 Written Opinion issued in International Patent Application No. PCT/FR2015/053258.
Feb. 3, 2016 Search Report issued in International Patent Application No. PCT/FR2015/053258.

* cited by examiner

*Primary Examiner* — Lori A. Clow
(74) *Attorney, Agent, or Firm* — Oliff PLC

(57) ABSTRACT

A method for determining a quantity $G_{inhib}$ quantifying the inhibitory capacity of a molecule on a type of microorganism includes: preparing a plurality of samples, including microorganisms of the type, a nutrient medium for the microorganism and an initial amount of the molecule per microorganism increasing in a range $[Q_{min}, Q_{max}]$ as a function of a classification of the samples; measuring the growth of the microorganisms in the samples as a function of time; and determining the quantity $G_{inhib}$ as a function of the measurements of the growth. Determination of the quantity $G_{inhib}$ includes: for each sample, calculating a value reflecting the growth of the microorganism of said type based on measurements of growth; classifying the values calculated for the samples as a function of the classification of the samples; and determining the quantity $G_{inhib}$ as a function of the variation of the classified values.

20 Claims, 12 Drawing Sheets

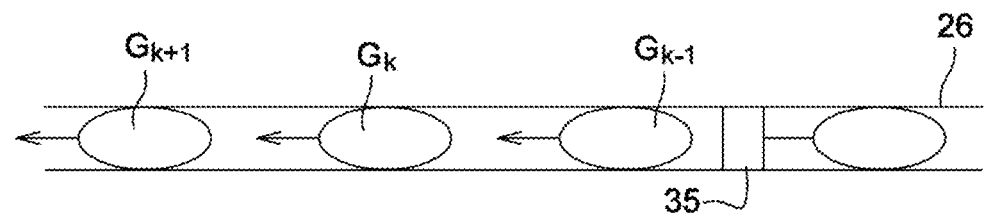
Fig. 3A
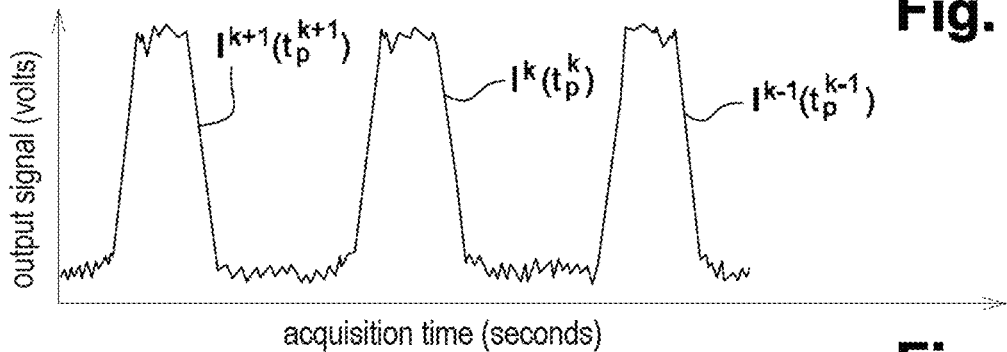
Fig. 3B
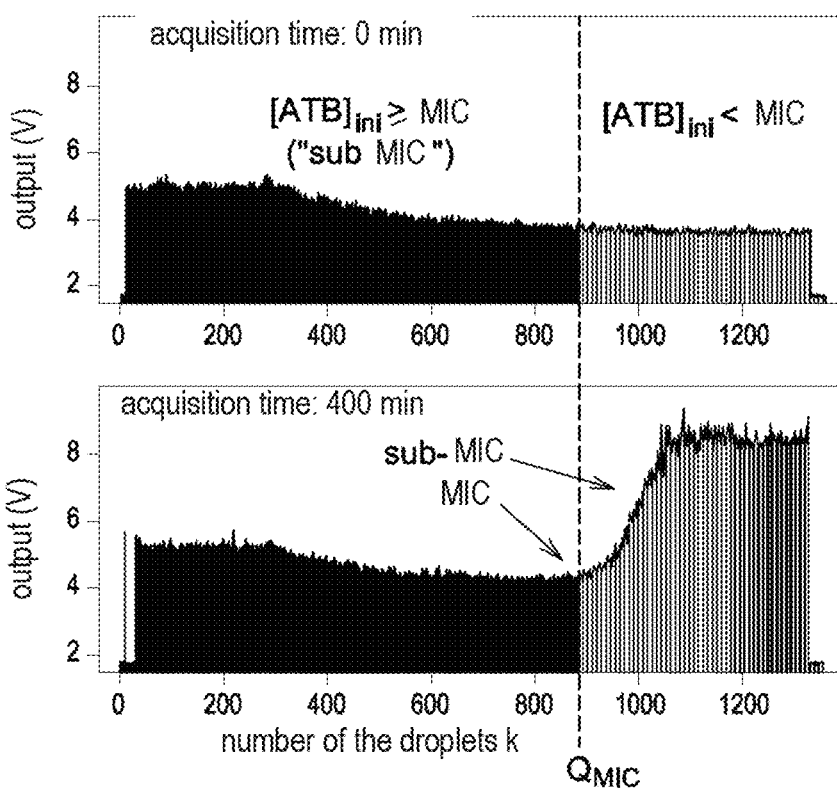
Fig. 4A
Fig. 4B

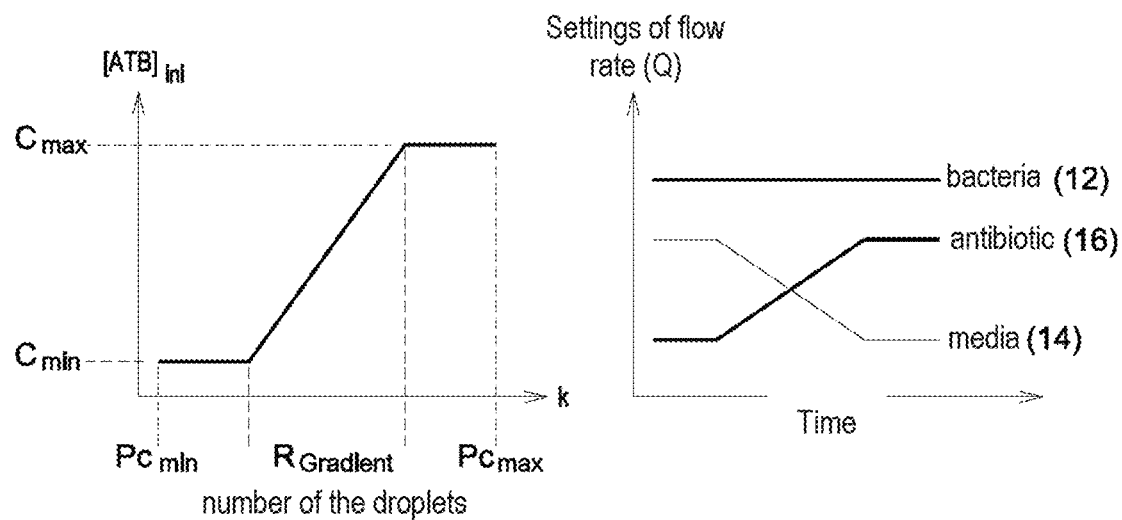
Fig. 8  Fig. 9
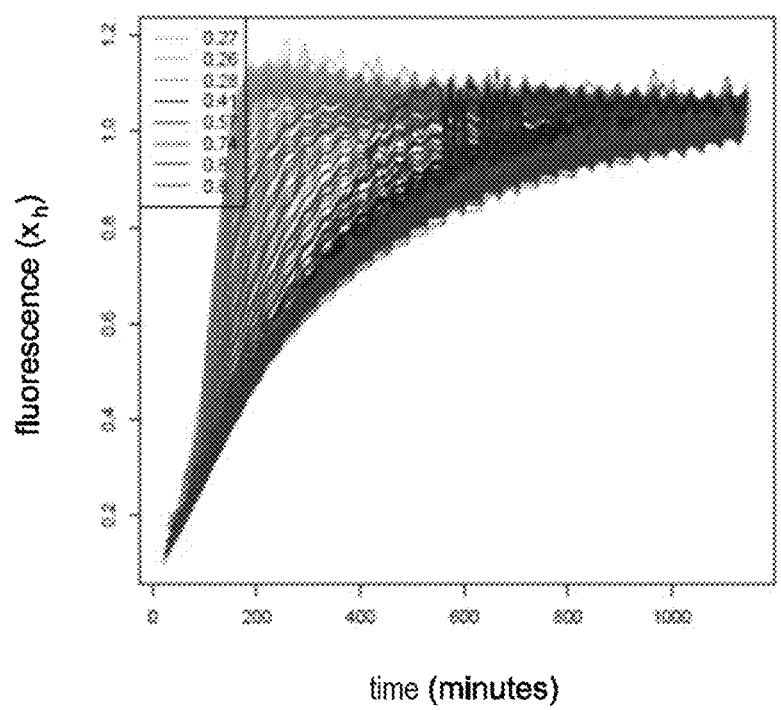
Fig. 10

METHOD AND DEVICE FOR CHARACTERIZING THE INHIBITORY CAPACITY OF A MOLECULE ON A MICROORGANISM

FIELD OF THE INVENTION

The invention relates to the field of analysis of the inhibitory capacity of a molecule on the growth of a microorganism, and notably the inhibitory capacity of an antibiotic on the growth of a bacterium and the inhibitory capacity of an antifungal on the growth of a yeast or mold.

PRIOR ART

The activity of an antibiotic on a bacterium is characterized notably by the "minimum inhibitory concentration", or MIC, which is defined as the minimum concentration of the antibiotic to be mixed with a population of the bacterium to inhibit its multiplication completely.

A first technique used for measuring the MIC consists, for a laboratory technician, of preparing several transparent-walled tubes comprising an initial concentration of the bacterium, said concentration being identical for all the tubes, a nutrient medium for the bacterium, and an initial concentration of antibiotic that increases as a function of the order of the tubes arranged in a rack. Once the tubes have been prepared with the concentration gradient of antibiotic, the technician then puts the tubes in an incubator. If the concentration of an antibiotic in a tube is too low to inhibit the growth of the bacteria, turbidity appears in the tube, the turbidity becoming greater as the bacterial population increases. After a given incubation time, the laboratory technician then inspects the tubes visually and identifies the MIC as being equal to the lowest concentration of antibiotic among the tubes that do not show any turbidity. The imprecise nature of such a method will readily be appreciated. Not only is the number of tubes prepared very small, usually less than 10, which does not give high accuracy for the MIC, but in addition identification of the latter depends on the judgment of a technician concerning the presence or absence of turbidity in a tube.

Devices and methods have therefore been developed for increasing both the precision for the concentration of antibiotic in a sample and the robustness of detection of bacterial growth in a sample. More particularly, devices are now capable of preparing a large quantity of bacterial samples, each of which may comprise their own concentration of antibiotic, and they are capable of measuring, automatically and accurately, a quantity that depends on the size of the bacterial population in a sample, for example fluorescence or optical density. Notably, the device described in the article "*Millifluidic droplet analyser for microbiology*" by L. Baraban et al., Lab on Chip, 2011, 11, 4057, produces a train of droplets with a volume under a microliter and whose composition of bacteria, nutrient medium and antibiotic can be adjusted precisely. Such a device notably makes it possible to produce a train of several hundred to several thousand droplets of constant volume and each comprising a fixed initial count of bacteria, and an initial concentration of antibiotic that decreases as a function of the position of the droplets in the train.

Referring to the schematic view in FIG. 1, this device 10 comprises, for production of the train of droplets:
three syringes 12, 14, 16, with a controllable flow rate and containing an aqueous solution of bacteria, an aqueous solution of nutrients and an aqueous solution of antibiotic, respectively. The syringes 12, 14, 16 inject their contents in a controlled manner into a junction 18, where they are mixed to form an aqueous solution; and
two syringes 20, 22, with a controllable flow rate and containing a first oil and a second oil, respectively, which are immiscible with the aqueous solution, and immiscible with one another. The contents of these syringes are injected at the level of a junction 24. This junction also receives the aqueous solution from junction 18 and opens into a transparent main tube 26. The first oil, for example of the hydrofluoroether type, notably HFE-7500®, serves as the continuous medium in which droplets of aqueous solution from junction 18 are deposited. The second, mineral, oil is used for forming elements for spacing the droplets. Notably, after each droplet of aqueous solution is formed in the first oil, a droplet of the second oil is deposited in the first oil.

Referring to FIG. 2, the syringes 12, 14, 16, 20, 22 are controlled by computer in order to obtain a train that is uniform with respect to both the volume and the spacing of droplets of bacterial solution in tube 26. FIG. 2 shows three droplets of bacterial solution $G_{k-1}$, $G_k$ and $G_{k+1}$ formed successively in the first oil 28 and separated from one another by spacing droplets $S_{k-1}$, $S_k$, $S_{k+1}$ consisting of the second oil. It should be noted in particular that the droplets $G_{k-1}$, $G_k$ and $G_{k+1}$ are referenced naturally by their position in the train of droplets, or equivalently by an integer, or index, k. The integer "1" thus corresponds to the droplet formed first in the train that is investigated by the analyzer. The contents of the first three syringes 12, 14, 16, under computer control, give droplets comprising:
an identical initial concentration of bacteria $[bact]_{ini}(k)$ =constant, as illustrated by curve 30, or a constant initial number $N_0$ of bacteria;
and an initial concentration of antibiotic $[ATB]_{ini}(k)$ that decreases as a function of the position k of the droplet in the droplet train, as illustrated by curve 32.

For the section for detection of the bacterial population in the droplets, device 10 comprises:
a secondary tube 28 parallel to the main tube 26, a controllable valve 30 for injecting the oil from syringe 20 either into tube 26 or into the secondary tube 28, and two valves 32, 34, arranged respectively at the beginning and at the end of the main tube 26 and controllable between an open position and a closed position. The valves 30, 32, 34, under computer control, thus make it possible to define two flows "A" and "B" in opposite directions in the main tube 26, and therefore a reciprocating motion 36 of the droplets in the transparent tube 26; and
a detection system 38, arranged opposite tube 26, for measuring the fluorescence of the droplets at a particular wavelength.

Notably, the bacteria contained in the droplets comprise a molecule that is fluorescent, either naturally, or artificially (for example by incorporating a gene encoding a fluorescent protein in the genome of the bacterium). As a variant, the nutrient medium of the droplets comprises an element that can be metabolized by the bacteria, in the form of a fluorescent molecule. The fluorescence of a droplet therefore depends directly on the number of bacteria it contains. The detection system 38 comprises a set of elements and circuits to form a light spot on the main tube 26 so as to excite the fluorescence wavelength of the fluorescent molecules, and measure the fluorescence induced by this excitation. Thus, referring to FIG. 3A, which illustrates a leftward movement of the droplets $G_{k-1}$, $G_k$ and $G_{k+1}$, each of them passes through the detection spot 35 of the system 38. The measurement signal induced by passage of the droplets $G_{k-1}$, $G_k$ and $G_{k+1}$ in front of the system 28 produces a signal as illustrated in FIG. 3B, namely a pulse train approximately in the form of strobe pulses $I^{k+1}(t_p^{k+1})$, $I^k(t_p^k)$, $I^{k-1}(t_p^{k-1})$.

The device 10 allows rapid passage of the set of droplets through spot 35. Passage of all the droplets through spot 35 may in fact take less than a minute. The frequency of the passages in front of spot 35 and/or the frequency of the measurements may for its part be controlled independently of the speed of the reciprocating motion. For bacteria, for example, the fluorescence of the droplets is measured about 8 times per hour or every 7 to 8 minutes for about 2 h to 16 h.

In operation, device 10 therefore produces a train of N droplets in the main tube 26, then the syringe 20 and the valves 30, 32 are controlled in order to produce a reciprocating motion of the droplets in tube 26 so that each of the droplets passes at regular intervals in front of the detector system 28, which measures its fluorescence. A measurement cycle thus consists of passage of the set of droplets through spot 35 for measuring them. During a measurement cycle "p", the droplets are measured at different time points, the time point of measurement of a droplet "k" being equal to $t_p^k$. Regarding the time point $t_p$, it is the time point of measurement of the last droplet during the p-th cycle, i.e. the time point of measurement $t_p^1$ or $t_p^N$ as a function of the direction of reciprocating motion during the p-th measurement cycle.

The measurement signal is then processed by computer to reduce each measured pulse $I^k(t_p^k)$ to a value $x^k(t_p^k)$, for example the mean value of the plateau of each pulse, and the values $x^k(t_p^k)$ thus produced are stored in the computer with their acquisition time point $t_p^k$. The values $x^k(t_p^k)$ are therefore representative of the quantity of bacteria contained in the droplets. For each droplet k, a set of measurements $\{x^k(t_1^k), x^k(t_2^k), \ldots, x^k(t_p^k) \ldots, x^k(t_P^k)\}$ is therefore produced, corresponding to the set of measurement time points $\{t_1^k, t_2^k, \ldots, t_p^k, \ldots, t_P^k\}$ up to the time point $t_P^k = t_p$. Notably, each acquisition time point $t_p^k$ corresponds to a particular incubation time of the droplets.

FIGS. 4A and 4B illustrate for example the values $x^k(t_p^k)$ as a function of the number k of droplets $k \in [1; N]$, respectively for the first measurement cycle and for a measurement cycle corresponding to $t_p = 400$ minutes. These figures correspond to the production of 1300 droplets each initially comprising 1000 E. coli bacteria with a concentration of antibiotic "cefotaxime" (or CTX) varying regularly from 0.0015 µg·mL$^{-1}$ to 0.03 µg·mL$^{-1}$, or a precision on the concentration below $10^{-4}$ µg·mL$^{-1}$. It can be seen from these figures that for some of the droplets, their measurements $x^k(t_p^k)$ increase relative to their respective initial time points $t_1^k$, which therefore indicates growth of the population of the bacteria that they contain and, as a corollary, that the initial concentration of antibiotic that they contain was insufficient to inhibit this growth completely. FIG. 5 illustrates the same phenomenon as a function of the set of measurement time points between 0 and 1400 minutes.

The minimum inhibitory concentration MIC is then determined by incubating the droplets for a time that is judged satisfactory, and then dividing the droplets of the last measurement cycle p into two sets, namely between those whose measurement signal $x^k(t_p^k)$ remains roughly identical to their initial signal $x^k(t_1^k)$ and those whose measurement signal $x^k(t_p^k)$ is greater than their initial signal $x^k(t_1^k)$. The number $k_{ini}$ is thus determined by dividing the droplets into these two sets. As the concentration gradient is defined as a function of the number k of the droplets, the MIC concentration is then equal to the initial concentration of antibiotic in the droplet of number $k_{ini}$.

The inventors conducted tests for determining the MIC concentrations using the device just described, and these tests are illustrated in FIGS. 6A-6C. The latter illustrate tests conducted on 5 replicates of a strain of E. coli ("replicate 1" to "replicate 5") in the presence of gentamicin (FIG. 6A), chloramphenicol (FIG. 6B) or nalidixic acid (FIG. 6C). In these figures, the abscissa shows the incubation time of the droplets (in minutes) and the ordinate shows the MIC concentration (in µg·mL$^{-1}$) determined by "cutting" the set of droplets as described above. A point of a curve, with coordinates (MIC$_p$, $t_p$), therefore represents determination of the MIC concentration as a function of the $x^k(t_p^k)$ values of the droplets acquired for the measurement cycle p. The strain of E. coli used for the tests is a known strain, of reference ATCC 25922, for which the MIC is known for the three antibiotics in question. The dotted line in these figures represents the MIC concentration recognized by the French government, or "regulatory" MIC (0.5 µg·mL$^{-1}$ for gentamicin, 4 µg·mL$^{-1}$ for chloramphenicol and 2 µg·mL$^{-1}$ for nalidixic acid) and the gray band around the regulatory MIC corresponds to the tolerance range for which measurement of the MIC by any technique is deemed to comply with the regulations. The regulatory MIC concentration is determined by the manual technique described above for an incubation time fixed by the regulations of from 18 to 24 h, and the tolerance range corresponds to a dilution +1/−1 around this concentration.

Based on these results, it will be noted in particular that there is no convergence of the MIC concentration determined by the "cutting" method, and it continues to increase for a long time. This behavior of the MIC concentration might partly be explained by the type of fluorescence detection used. In fact, in the context of a bacteriostatic antibiotic, when the fluorescence measured is that of molecules rejected by the bacteria following digestion of the nutrient medium, the quantity of these molecules may increase whereas the bacterial count remains stable. However, this would only very partially explain the behavior of the MIC concentration. Without being bound to any theory, the inventors think that devices such as that described above reveal phenomena that were masked by the reference technique for determination of the MIC concentration. A precise and robust determination of the "true" minimum inhibitory concentration (as opposed to the "regulatory" MIC) as a function of the data produced by a device as accurate as that described in the article "*Millifluidic droplet analyser for microbiology*", or of any other similar device capable of producing a large number of "incubators" by precisely controlling their initial contents, therefore raises further problems, and is therefore difficult in practice.

This same finding will also apply to any quantity used for characterizing the inhibitory capacity of a molecule on microorganisms (bacteria, yeast, mold, etc.), for example the growth rate of the bacteria, the lag phase of growth, the maximum bacterial count by volume, the concentration ranges of antibiotics that are partially inhibitory, etc.

SUMMARY OF THE INVENTION

The aim of the present invention is to solve the aforementioned problem by proposing a more robust and more precise determination of the inhibitory capacity of a molecule on a microorganism, for example the true MIC concentration.

For this purpose, the invention relates to a method for determining a quantity $G_{inhib}$ quantifying the inhibitory capacity of a molecule on a microorganism of a predetermined type, comprising:

preparing a plurality of samples, each comprising at least one microorganism of said type, a nutrient medium for the microorganism and an initial amount of the molecule per microorganism of said type present in the sample, said initial amount increasing in a range $[Q_{min}, Q_{max}]$ as a function of a predetermined classification of the samples;

incubating the samples;

for each sample, measuring the growth of the microorganisms in the sample as a function of time for a predetermined incubation time; and determining the quantity $G_{inhib}$ as a function of the measurements of the growth of the microorganisms in the samples, According to the invention, determination of the quantity $G_{inhib}$ comprises:

for each sample, calculating a value reflecting the growth of the microorganism of said type as a function of the measurement of growth of the microorganisms in the sample;

classifying the values calculated for the samples as a function of the classification of the samples; and determining the quantity $G_{inhib}$ as a function of the variation of the classified values.

In other words, determination of the quantity $G_{inhib}$ is not performed on the values $x^k(t_P^k)$, or any other quantities directly related to them, for example the size of the bacterial population calculated as a function of these values for a time $t_P$ or a given cycle P. Information on the dynamics of growth of the bacteria is firstly determined as a function of the values $\{x^k(t_1^k), x^k(t_2^k), \ldots, x^k(t_p^k) \ldots, x^k(t_P^k)\}$ and it is this information that is then processed to determine the quantity $G_{inhib}$.

This information is sought advantageously on the basis of prior knowledge of the behavior of the bacteria, notably using a growth model for which we identify at least one of the parameters containing information about the dynamics of growth. As will be presented in detail hereunder, determination of the quantity $G_{inhib}$ then takes place quickly, more precisely and reproducibly. Moreover, the whole process is automated and therefore less dependent on interpretation by the operators.

According to one embodiment:
the growth of the microorganism is modeled by a model of growth as a function of time comprising:
a first lag phase of duration $\lambda$;
followed by a second exponential growth phase of maximum slope $\mu$ in the logarithmic space; and
followed by a third stationary phase of maximum value A;

and the value reflecting the growth of the microorganism of said type as a function of time is an estimate of the maximum slope $\mu$ and/or an estimate of the duration of the lag phase $\lambda$.

In other words, the growth profile corresponds to that proposed by Rosso L. in the thesis "*Modeling and predictive microbiology: development of a new tool for the food-processing industry.*" Doctorate thesis, University Claude Bernard Lyon 1, 1995. The slope $\mu$ and the lag phase $\lambda$ are in fact each directly linked to the dynamics of growth of the bacteria.

According to one embodiment:
the quantity $G_{inhib}$ comprises a range $[Q_{min}^{MIC}, Q_{max}^{MIC}]$ for which growth of the microorganisms in the samples is at least partially inhibited;
the initial amount of the molecule as a function of the classification of the samples comprises:
a first part that is constant for several samples and equal to $Q_{min}$, the lower limit $Q_{min}$ of the range $[Q_{min}, Q_{max}]$ being selected so that there is no inhibition of the growth of the microorganisms in the samples;
followed by a second part strictly increasing from $Q_{min}$ to $Q_{max}$;
followed by a third part that is constant for several samples and equal to $Q_{max}$, the upper limit $Q_{max}$ of the range $[Q_{min}, Q_{max}]$ being selected so that there is complete inhibition of the growth of the microorganisms in the samples;
and determination of the range $[Q_{min}^{MIC}, Q_{max}^{MIC}]$ comprises:
identifying a transition zone in the variation of the values classified between two roughly stationary extreme zones of said variation; and
determining the range $[Q_{min}^{MIC}, Q_{max}^{MIC}]$ as being the range corresponding to the samples of the transition zone identified.

In other words, owing to the particular design of the samples, it is possible to identify more easily the range $[Q_{min}^{MIC}, Q_{max}^{MIC}]$ in which. This range, which is the transition zone of the inhibitory effect of the molecule, between no inhibitory effect and a complete inhibitory effect, is in itself a useful quantity $G_{inhib}$ and further comprises other types of useful information, for example the MIC concentration.

Notably, identification of the transition zone comprises determination of two inflexion points of the variation of the classified values, the transition zone being bounded by the two inflexion points determined. Notably, identification of the transition zone comprises modeling the variation of the classified values by a piecewise linear continuous function comprising only two extreme straight-line segments and an intermediate straight-line segment between the two extreme straight-line segments, the intermediate straight-line segment being the transition zone.

According to an advantageous embodiment, the quantity $G_{inhib}$ comprises a minimum initial quantity of molecules $Q_{MIC}$ that completely inhibits the growth of the microorganisms, said initial minimum inhibitory amount $Q_{MIC}$ being selected equal to the upper limit $Q_{max}^{MIC}$ of the range $[Q_{min}^{MIC}, Q_{max}^{MIC}]$.

According to one embodiment, the lower limit $Q_{min}$ of the range $[Q_{min}, Q_{max}]$ is a zero quantity of the molecule, for example an antibiotic.

According to one embodiment:
the measurements of the growth of the bacteria in the samples and determination of the quantity $G_{inhib}$ as a function of said measurements are performed for increasing incubation times so as to obtain a sequence of quantities $G_{inhib}$ as a function of the incubation time of the samples;
the method comprises analysis of the stability of said sequence as a function of the incubation time; and
the quantity $G_{inhib}$ is the value of the sequence once the sequence has stabilized.

In other words, the invention makes it possible to determine a sequence corresponding to the quantity $G_{inhib}$ that is convergent, which makes it possible to employ a stability test, and therefore a test allowing detection and automatic stopping of incubation and/or of data processing. Notably, the accuracy of the estimate increases with the length of the sequence.

According to one embodiment, the samples each comprise initially at least 100 microorganisms, and preferably at least 500 microorganisms. In other words, providing a minimal initial number of bacteria avoids exacerbating the particular features of a particular bacterium. Of course, owing to the invention, it is also possible to study a smaller population, or even one microorganism if we wish to know the effect of the molecule on this microorganism in particular, such as for studying the phenomena of hetero-resistance of a bacterium, for example.

According to one embodiment, the samples each comprise an initial amount of a different second molecule capable of inhibiting the growth of the microorganisms, notably an identical initial amount for all the samples. In other words, the invention makes it possible to study the synergy effects between inhibitors, for example antibiotics.

According to one embodiment, the minimum amount of the molecule per microorganism of said type is a concentration of the molecule in the samples, the initial concentration of microorganism of said type in the samples being constant as a function of the classification of the samples.

According to one embodiment, the microorganism is a bacterium, and the molecule is an antibiotic. As a variant, the microorganism is a yeast or a mold, and the molecule is an antifungal.

According to one embodiment, the nutrient medium comprises an element that can be metabolized by the microorganism in the form of a fluorescent molecule, and measurement of the growth of the microorganisms in the samples is a measurement of the fluorescence of the samples. As a variant, the absorbance of the samples is variable as a function of the quantity of microorganisms present in the latter, and in that measurement of the growth of the microorganisms in the samples is a measurement of optical density.

According to one embodiment, preparation of the plurality of samples comprises preparation of a train of droplets forming samples in oil.

The invention also relates to a device for estimating a quantity $G_{inhib}$ by quantifying the inhibitory capacity of a molecule on a microorganism of a predetermined type, comprising:
  means for preparing a plurality of samples, each comprising at least one microorganism of said type, a nutrient medium for the microorganism and an initial amount of the molecule per microorganism of said type present in the sample, said initial amount increasing in a range $[Q_{min}, Q_{max}]$ as a function of a predetermined classification of the samples;
  means for incubating the samples;
  means for measuring the growth of the microorganisms in each sample as a function of time for a predetermined incubation time; and
  calculating means for determining the quantity $G_{inhib}$ as a function of the measurements of the growth of the microorganisms in the samples, According to the invention, the calculating means are able to carry out:
  for each sample, calculation of a value of a parameter of a parametric model of growth of the microorganism of said type as a function of the measurement of growth of the microorganisms in the sample;
  classification of the values calculated for the samples as a function of the classification of the samples; and
  determination of the quantity $G_{inhib}$ as a function of the variation of the classified values.

Notably, the device is able to carry out a method of the aforementioned type.

BRIEF DESCRIPTION OF THE FIGURES

The invention will be better understood on reading the description given hereunder, supported by the appended figures, in which:
FIG. 3 is a scheme describing the production of fluorescence signals by the analyzer of FIG. 1;
FIGS. 4A and 4B are plots of fluorescence measurements as a function of the number of the droplets produced, at 0 minute and 400 minutes, respectively;
FIG. 8 is a diagram illustrating an initial concentration profile of antibiotic in the droplets generated during the method according to the invention;
FIG. 9 is a diagram illustrating settings of flow rate of the syringes of the analyzer of FIG. 1, generated as a function of the profile in FIG. 8;
FIG. 10 is a plot of the fluorescence measurements of the droplets produced by the settings in FIG. 9 as a function of time.

DETAILED DESCRIPTION OF THE INVENTION

Embodiment Example

Figure 1:
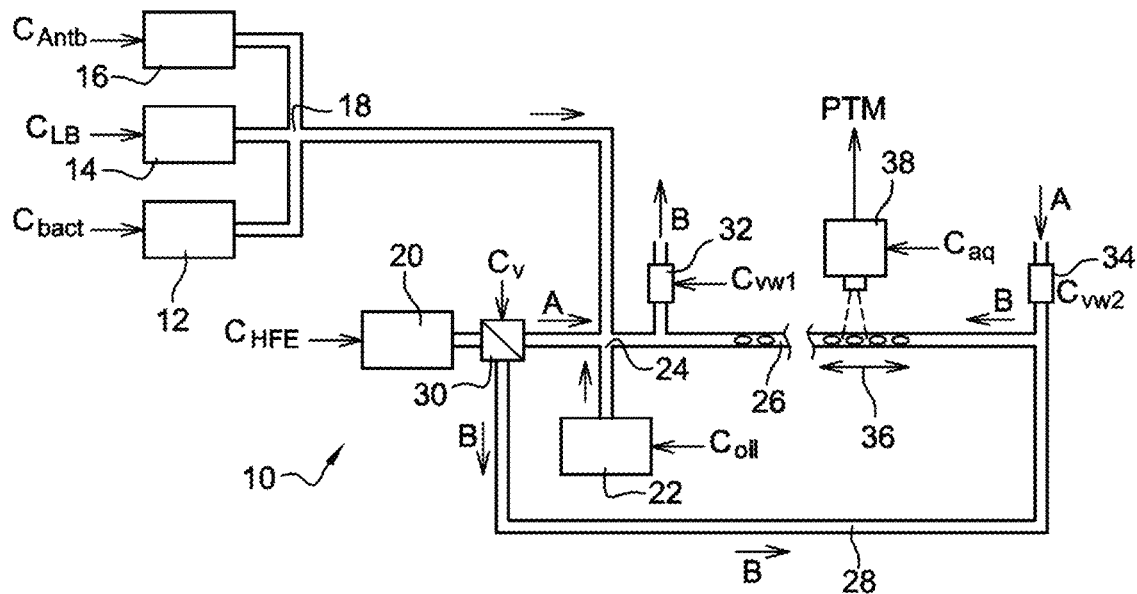
FIG. 1 is a simplified schematic view of the analyzer described in the article "*Millifluidic droplet analyser for microbiology*"
Figure 2:
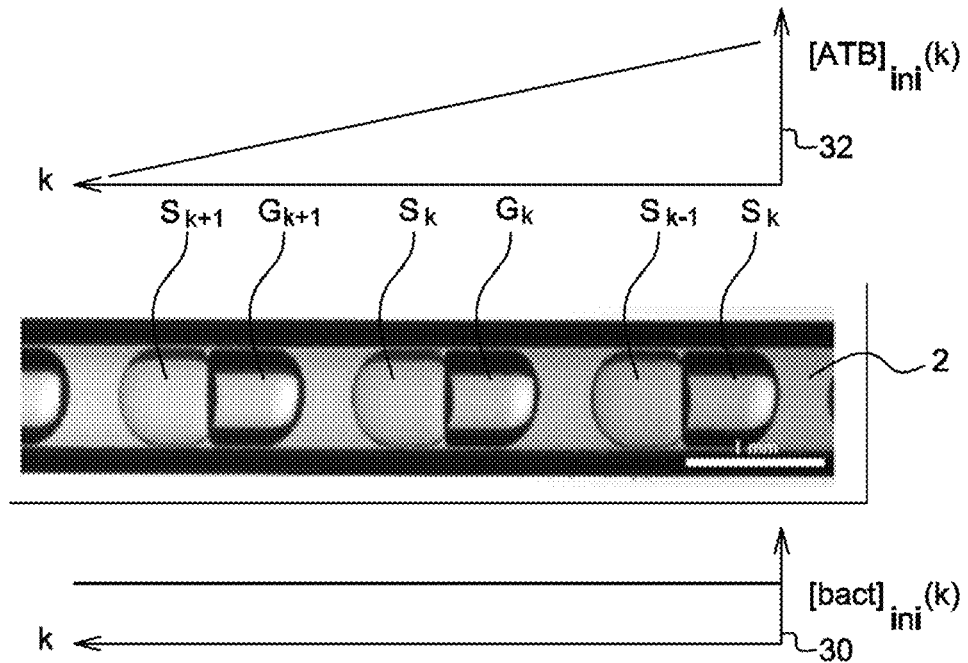
FIG. 2 is an example of droplets produced by the analyzer of FIG. 1.
Figure 5:
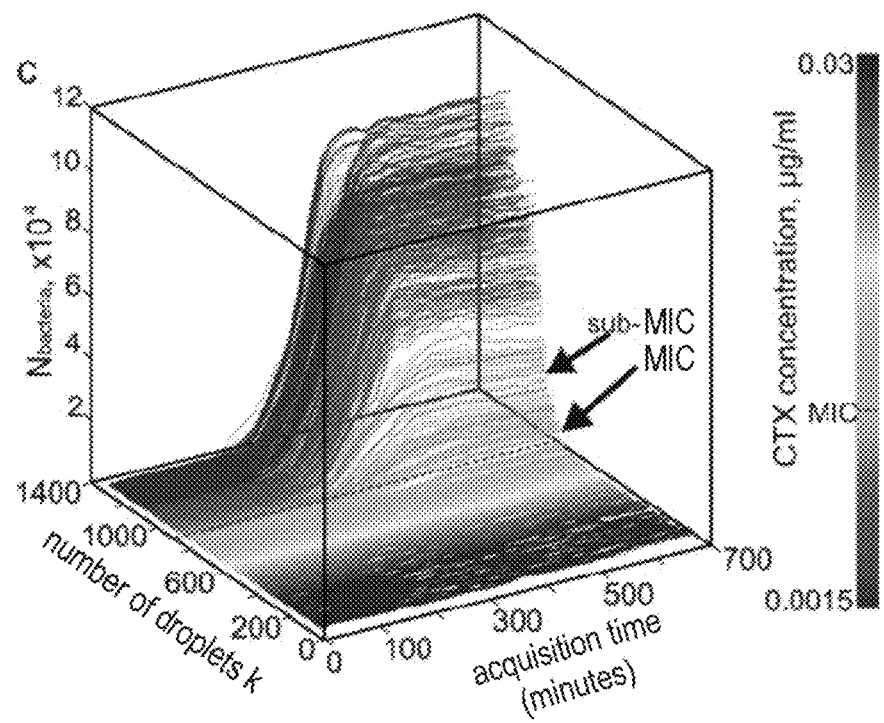
FIG. 5 is a plot of fluorescence measurements as a function of the number of the droplets produced and time.
Figure 7:
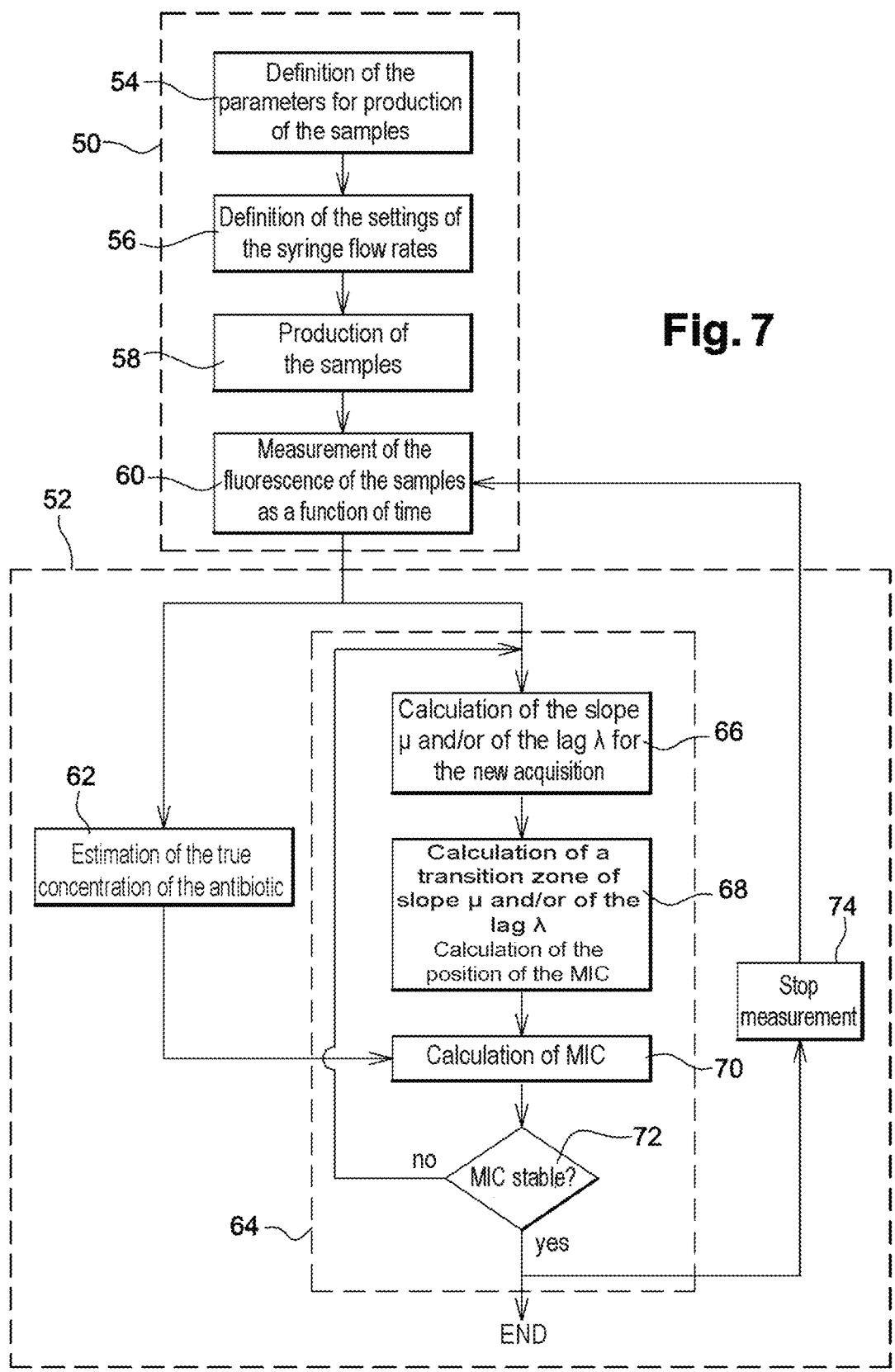
FIG. 7 is a flowchart of one embodiment of the method according to the invention.

An embodiment of the method according to the invention will now be described in relation to the flowchart in FIG. 7, steps of this method being illustrated in FIGS. 8 to 19. The method is applied for determination of a minimum inhibitory concentration MIC of the growth of bacteria, by means of the device 10 described in the article "*Millifluidic droplet analyser for microbiology*" and briefly described above in relation to FIG. 1. Control of the components of this device and processing of the measurements are performed by means of a conventional data processing unit, for example a computer.

The method comprises the production, at 50, of experimental data on the growth of bacteria in the presence of a gradient of antibiotic, and analysis, at 52, of the data produced to determine the MIC concentration.

The production step 50 comprises a first step 54 of determining parameters for production of the data. Step 54 notably comprises definition of a concentration range $[C_{min}; C_{max}]$ which is assumed to include the MIC concentration, namely $C_{min} < MIC < C_{max}$. This range is determined as a function of preceding studies, notably as a function of a regulatory MIC concentration or clinical studies. Notably, the concentration $C_{max}$ is a concentration for which the antibiotic completely inhibits bacterial growth and is above the MIC concentration. As a variant, the method described below serves for adjusting the range $[C_{min}; C_{max}]$. For example, if the MIC concentration determined is very far from the maximum concentration $C_{max}$, the latter is decreased and the method is carried out once more. Similarly, if the MIC concentration is too close to the maximum concentration $C_{max}$, the latter is increased and the method is restarted. Preferably, the minimum concentration $C_{min}$ is selected so as to guarantee that the bacteria are more or less free to grow, said free growth being exploited subsequently in data processing, as will be explained in more detail below. For example, the concentration $C_{min}$ is equal to 0.

An initial concentration profile of antibiotic $[ATB]_{ini}$ as a function of the number k of the droplets subsequently produced is then generated as illustrated in FIG. 8. This profile comprises:
- a first plateau $P_{C_{min}}$ for which $\forall k \in [1; N_{C_{min}}]$, $[ATB]_{ini}(k) = C_{min}$;
- followed by a ramp $R_{gradient}$ for which the concentration $[ATB]_{ini}(k)$ increases linearly from the minimum concentration $C_{min}$ to the maximum concentration $C_{max}$, i.e. $\forall k \in [N_{C_{min}}+1; N_{gradient}]$, $[ATB]_{ini}(k+1) - [ATB]_{ini}(k) = $ constant;
- followed by a second plateau $P_{C_{max}}$ for which $\forall k \in [N_{gradient}; N]$, $[ATB]_{ini}(k) = C_{max}$.

The lengths of the plateaux $P_{C_{min}}$ and $P_{C_{max}}$ are selected so as to identify automatically portions of straight lines with roughly zero slope as a function of the number k in the data produced subsequently. These lengths depend for example on the accuracy of the algorithm used. The inventors noted, however, that a plateau length equal to about a hundred droplets allows good-quality identification. Regarding the length of the ramp $R_{gradient}$, it is defined as a function of the desired precision for the MIC concentration, in the limits imposed by the device for producing the droplets.

Flow rate settings for the syringes 12, 14, 16 are then produced, at 56, as a function of the initial concentration profile of antibiotic $[ATB]_{ini}$. These settings are illustrated in FIG. 9. Notably, the flow rate setting of syringe 12 of bacterial solution is constant in order to produce droplets comprising roughly the same initial number of bacteria. This number is advantageously greater than 500 so as not to exacerbate the particular features of each bacterium, for example 1000 bacteria. The flow rate setting of syringe 16 of antibiotic for its part follows the profile $[ATB]_{ini}$ and the flow rate setting of syringe 18 of nutrient medium has an inverted profile in order to produce droplets of constant volume.

In parallel, the solutions of bacteria, of nutrient medium and of antibiotic are prepared and then put in their respective syringes. Advantageously, and optionally, a fluorescent marker, for example sulforhodamine, of known concentration, is also added to the antibiotic solution. This marker, whose fluorescence is measurable by the detection system 28, advantageously at a wavelength different than that used for measuring the population of the bacteria, makes it possible to determine the true concentration of antibiotic in each droplet, as will be explained in detail below. This additional fluorescence is measured by the detection system 38, which is equipped for example with a set of filters for selecting the measured wavelength, as described for example in the document "*Millifluidic droplet analyser for microbiology*".

Figure 11:
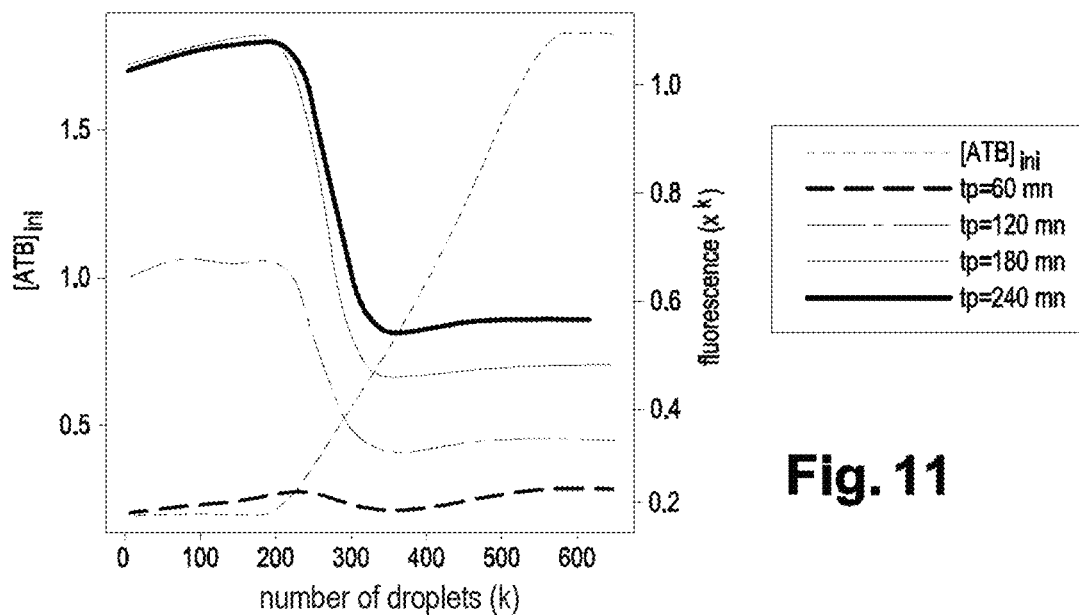
FIG. 11 is a diagram illustrating measurements of fluorescence as a function of the number of the droplets for different measurement time points.

In a next step 60, the device 10 is controlled as a function of the flow rate settings thus defined in order to produce a train of N droplets, and the fluorescence of each droplet is measured regularly using the reciprocating motion described above. Still at 60, the measurement signal from the detection system 28 is processed to produce and store the fluorescence values $\{x^k(t_1^k), x^k(t_2^k), \ldots, x^k(t_p^k), \ldots, x^k(t_P^k)\}$ of each droplet for the acquisition time points $\{t_1^k, t_2^k, \ldots, t_p^k, \ldots, t_P^k\}$. An example of quantities $x^k(t_p^k)$ is illustrated in FIGS. 10 and 11, either as a function of time $t_p^k$ (FIG. 10) or as a function of the number of the droplets for different measurement cycles (FIG. 11).

For its part, the data processing step 52 comprises estimation, at 62, of the true initial concentration of antibiotic in the droplets. In practice, there is a difference between the flow rate settings and the true flow rates so that there is a difference between the desired profile $[ATB]_{ini}$ and the true concentration profile. Notably, the true profile may not be perfectly linear. The true concentration of antibiotic is estimated from the measured fluorescence of sulforhodamine $\{z^1(t_L^1), z^2(t_L^2), \ldots, z^k(t_L^k), \ldots, z^N(t_L^N)\}$ at the start of incubation of the droplets. The measurement cycle L is notably within the lag phase of the bacteria, and is for example the first measurement cycle. At this time point, the bacteria have not begun to grow and they induce a constant or zero fluorescence in the droplets. The variation of the fluorescence among the values $\{z^1(t_L^1), z^2(t_L^2), \ldots, z^k(t_L^k), \ldots, z^N(t_L^N)\}$ therefore corresponds to the fluorescence of the sulforhodamine added to the solution of antibiotic. Knowing the concentration of sulforhodamine, the fluorescence of the latter is therefore proportional to the initial concentration of the antibiotic $[ATB]_{ini}$.

The estimate $\widehat{[ATB]}_{ini}$ of the true concentration is calculated notably by:
applying a smoothing filter on the measurements $\{z^1(t_L^1), z^2(t_L^2), \ldots, z^k(t_L^k), \ldots, z^N(t_L^N)\}$, for example a standard Loess smoothing filter, so as to obtain smoothed measurements $\{\bar{z}^1, \bar{z}^2, \ldots, \bar{z}^k, \ldots, \bar{z}^N\}$;

identifying the start and end of the antibiotic gradient in the smoothed measurements. For example, the minimum value $z^{N_{min}} = \min\{\bar{z}^1, \bar{z}^2, \ldots, \bar{z}^k, \ldots, \bar{z}^N\}$ of the smoothed measurements is identified and the start of the gradient is identified as the smallest number $N_g^{min} > N_{min}$ of the droplet whose smoothed measurement $\bar{z}^{N_g^{min}}$ is X % higher than the value $z^{N_{min}}$, for example 1% higher. Similarly, the maximum value $z^{N_{max}} = \max\{\bar{z}^1, \bar{z}^2, \ldots, \bar{z}^k, \ldots, \bar{z}^N\}$ of the smoothed measurements is identified and the end of the gradient is identified as the largest number $N_g^{max} < N_{max}$ of the droplet whose smoothed measurement $\bar{z}^{N_g^{max}}$ is X % lower than the value $z^{N_{max}}$, for example 99%. Of course, any method for determining the start and end of the gradient may be used;

putting:

$$[\widehat{ATB}]_{ini}(k) = \begin{cases} C_{min} & \forall k \in [1; N_g^{min}[ \\ a \cdot \bar{z}^k + b & \forall k \in [N_g^{min}; N_g^{max}] \\ C_{max} & \forall k \in [N_g^{max}+1; N] \end{cases} \quad (1)$$

with $$a = \frac{C_{max} - C_{min}}{\bar{z}^{N_g^{max}} - \bar{z}^{N_g^{min}}} \text{ and } b = \frac{C_{max} + C_{min}}{2} - a \times \frac{\bar{z}^{N_g^{max}} + \bar{z}^{N_g^{min}}}{2}.$$

The estimated concentration $[\widehat{ATB}]_{ini}(k)$ is stored for later use as described above.

Figure 12A:
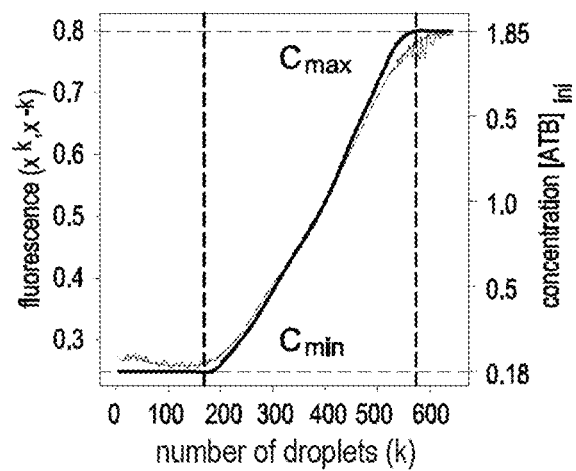
FIGS. 12A and 12B are diagrams illustrating estimation of the true initial concentration of antibiotic in the droplets for two different tests.
Figure 12B:
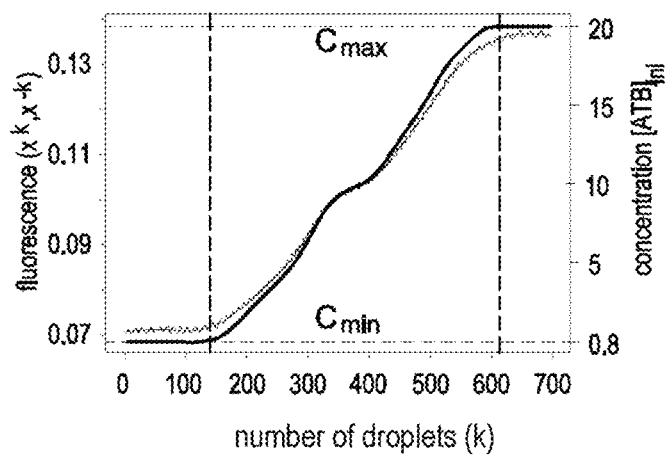

The known concentrations $C_{min}$ and $C_{max}$ thus serve as an anchorage point for linear transformation of the fluorescence gradient within the range $[\bar{z}^{N_g^{min}}; \bar{z}^{N_g^{max}}]$ into a concentration gradient $[\widehat{ATB}]_{ini}$ in the range $[C_{min}; C_{max}]$. Notably, this makes it possible to preserve the nonlinearities of the true profile of initial concentration induced by the errors in production of the droplets. FIGS. 12A and 12B illustrate estimation of the concentration profile $[ATB]_{ini}$ for two experiments conducted for two strains of *E. coli* respectively. The noisy curves represent the measured fluorescence $\{z^1(t_L^1), z^2(t_L^2), \ldots, z^k(t_L^k), \ldots, z^N(t_L^N)\}$, the smoothed curves (in bold) superimposed on the noisy curves correspond to the smoothed fluorescence $\{\bar{z}^1, \bar{z}^2, \ldots, \bar{z}^k, \ldots, \bar{z}^N\}$, and the curves anchored on the values $C_{min}$ and $C_{max}$ (shown with thin lines) are the estimated concentration $[\widehat{ATB}]_{ini}$. These figures, and particularly FIG. 12B, show the considerable nonlinearity of the measured fluorescence, caused by the imperfections of the device 10, and the estimate $[\widehat{ATB}]_{ini}$ of the concentration, which reproduces, to within a scaling factor, the fluorescence profile.

The processing 52 also comprises a step 64 carried out in parallel with the measurement step 60, namely each time a new measurement cycle P delivers new measurements $\{x^1(t_P^1) \, x^2(t_P^2), \ldots, x^k(t_P^k), \ldots, x^N(t_P^N)\}$ of the fluorescence of the droplets, for as long as a stop criterion described below is not satisfied. When step 64 is triggered, measurements $\{x^k(t_1^k) \, x^k(t_2^k), \ldots, x^k(t_p^k), \ldots, x^k(t_{P-1}^k)\}$, corresponding to the preceding measurement cycles 1, 2, ..., P−1, have therefore already been stored for each droplet k.

More particularly, for each droplet k, step 64 comprises a first step 66 of transforming the sequence $\{x^k(t_1^k) \, x^k(t_2^k), \ldots, x^k(t_p^k), \ldots, x^k(t_P^k)\}$, derived from concatenation of the stored sequence $\{x^k(t_1^k) \, x^k(t_2^k), \ldots, x^k(t_p^k), \ldots, x^k(t_{P-1}^k)\}$ with the new fluorescence measurement $x^k(t_P^k)$ of the droplet, into a value $D^k(t_P)$ containing information about the dynamics of growth of the bacteria in the droplet k for an incubation period between $t_1$ and $t_P$. The objective of this transformation is to take into account, for the measurement cycle of time point $t_P$, the history of the fluorescence up to execution of this cycle, while qualifying this history qualitatively, advantageously via a growth model.

Figure 13:
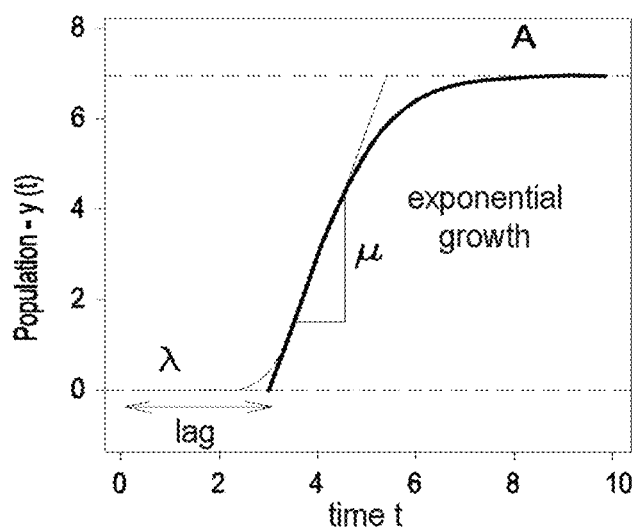
FIG. 13 is a diagram illustrating bacterial growth in the presence of nutrients and as a function of time.

This history is advantageously taken into account by means of a model of the growth of bacteria in a nutrient medium, more preferably the model in FIG. 13, which illustrates the natural logarithm of the bacterial population as a function of time. As is known, the growth of bacteria comprises:

a first lag phase of duration λ during which the bacteria synthesize enzymes that they will need in order to use the nutrient medium, and in which there is no cell division of the bacteria;

followed by an exponential growth phase: after an acceleration, the growth reaches a maximum growth rate μ, or equivalently, the growth curve has a maximum slope μ;

followed by a stationary phase, which corresponds to exhaustion of the nutrient medium. Growth slows down and becomes roughly zero, the bacterial population being roughly stabilized at a value A. The stationary phase is followed by a phase of decline, not shown here, following complete exhaustion of the nutrients.

The lag, growth and stationary phases are estimated for example by one and/or other of the temporal models y(t) in the following table:

| Name of the model | Formula y(t) | Parameters to be identified |
|---|---|---|
| Logistic | $y(t) = \dfrac{A}{1 + \exp\left(\dfrac{4 \cdot \mu}{A} \cdot (\lambda - t) + 2\right)}$ | A, μ, λ |
| Gompertz | $y(t) = A \cdot \exp\left(-\exp\left(\dfrac{\mu \cdot e}{A} \cdot (\lambda - t) + 1\right)\right)$ | A, μ, λ |

-continued

| Name of the model | Formula y(t) | Parameters to be identified |
|---|---|---|
| Modified Gompertz | $y(t) = A \cdot \exp\left(-\exp\left(\frac{\mu \cdot e}{A} \cdot (\lambda - t)\right) + 1\right) + A \cdot \exp(\alpha \cdot (t - t_{shift}))$ | $A, \mu, \lambda, \alpha, t_{shift}$ |
| Richards | $y(t) = A \cdot \left(1 + v \cdot \exp\left(1 + v + \frac{\mu}{A} \cdot (1+v)^{1+\frac{1}{v}}\right) \cdot (\lambda - t)\right)^{\left(-\frac{1}{v}\right)}$ | $A, \mu, \lambda, v$ | where e is Euler's constant.

For each measurement cycle P and for each droplet k, step 66 thus consists of identifying at least one of the parameters of a model y(t) containing information on dynamics as a function of the measured fluorescences $\{x^k(t_1^k), x^k(t_2^k), \ldots, x^k(t_p^k), \ldots, x^k(t_P^k)\}$ for the droplet, and notably a maximum slope $\mu^k(t_P)$ and/or a lag time $\lambda^k(t_P)$ for this sequence ($D^k(t_P)=\mu^k(t_P)$ or $D^k(t_P)=\lambda^k(t_P)$). Identification of the parameters of the model (t), which consists of minimizing an estimation error formed from the difference between the vector of the measurements $(x^k(t_1^k)\ x^k(t_2^k)\ \ldots\ x^k(t_p^k)\ \ldots\ x^k(t_P^k))^T$ and the vector of estimation of the measurements $(y(t_1^k)\ y(t_2^k)\ \ldots\ y(t_p^k)\ \ldots\ y(t_P^k))^T$, is performed in a manner known per se from the domain of the identification, for example by nonlinear least squares.

As a variant, the parameters are identified without using a model y(t), for example by calculating a polynomial by the method of splines approximating the sequence $(x^k(t_1^k)\ x^k(t_2^k)\ \ldots\ x^k(t_p^k)\ \ldots\ x^k(t_P^k))$. The parameters $\lambda$ and $\mu$ are then estimated empirically, for example by the finite-difference method. For example, the maximum slope $\mu$ is obtained by calculating the derivative of the polynomial approximating the sequence and selecting the maximum value of the derivative as the slope $\mu$. As another variant, the models or the approaches may be mixed.

Identification of the parameters of the growth of a bacterial population is well known from the prior art. For example, this identification may be performed using the "grofit" software package described in the document by Kahm M. et al. "grofit: Fitting Biological Growth Curve with R", Journal of Statistical Software, Vol. 33(7), February 2010.

As the calculation of the parameters is of a statistical nature, identification is preferably carried out once a minimum number of measurements have been acquired. The minimum number of measurement cycles is for example equal to 10, step 64 therefore being carried out for measurement cycles once this minimum number is reached.

At the end of step 66 of calculation of the parameters of growth of the bacteria, the following sequences are therefore produced:

$$M(t_P) = \{\mu^1(t_P), \mu^2(t_P), \ldots, \mu^k(t_P), \ldots, \mu^N(t_P)\}$$

$$\Lambda(t_P) = \{\lambda^1(t_P), \lambda^2(t_P), \ldots, \lambda^k(t_P), \ldots, \lambda^N(t_P)\}$$

Figure 14:
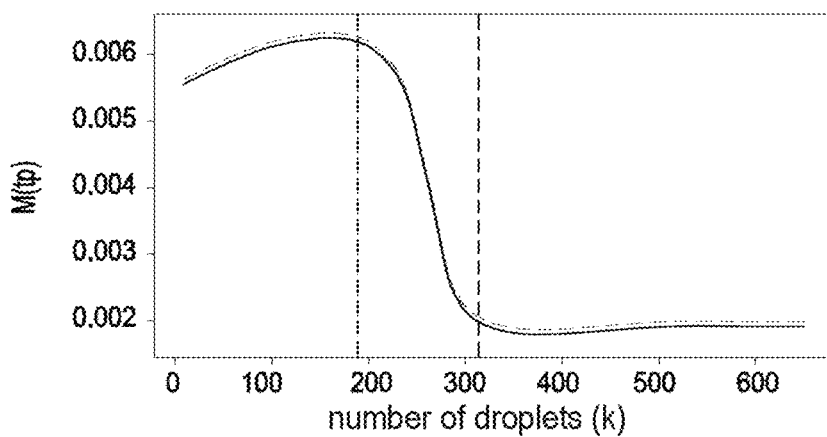
FIG. 14 is a diagram illustrating transformation of the fluorescence measurements into a sequence of maximum growth rates of the bacteria as a function of the number of the droplets.
Figure 15:
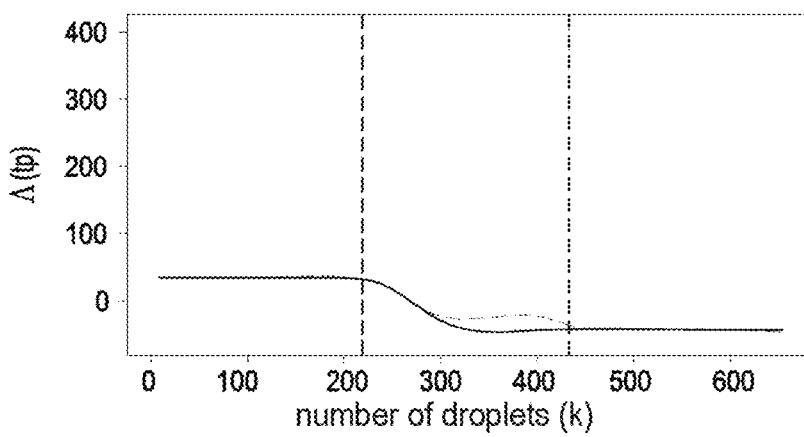
FIG. 15 is a diagram illustrating transformation of the fluorescence measurements into sequences of lag phase times of the growth of the bacteria as a function of the number of the droplets.
Figure 16:
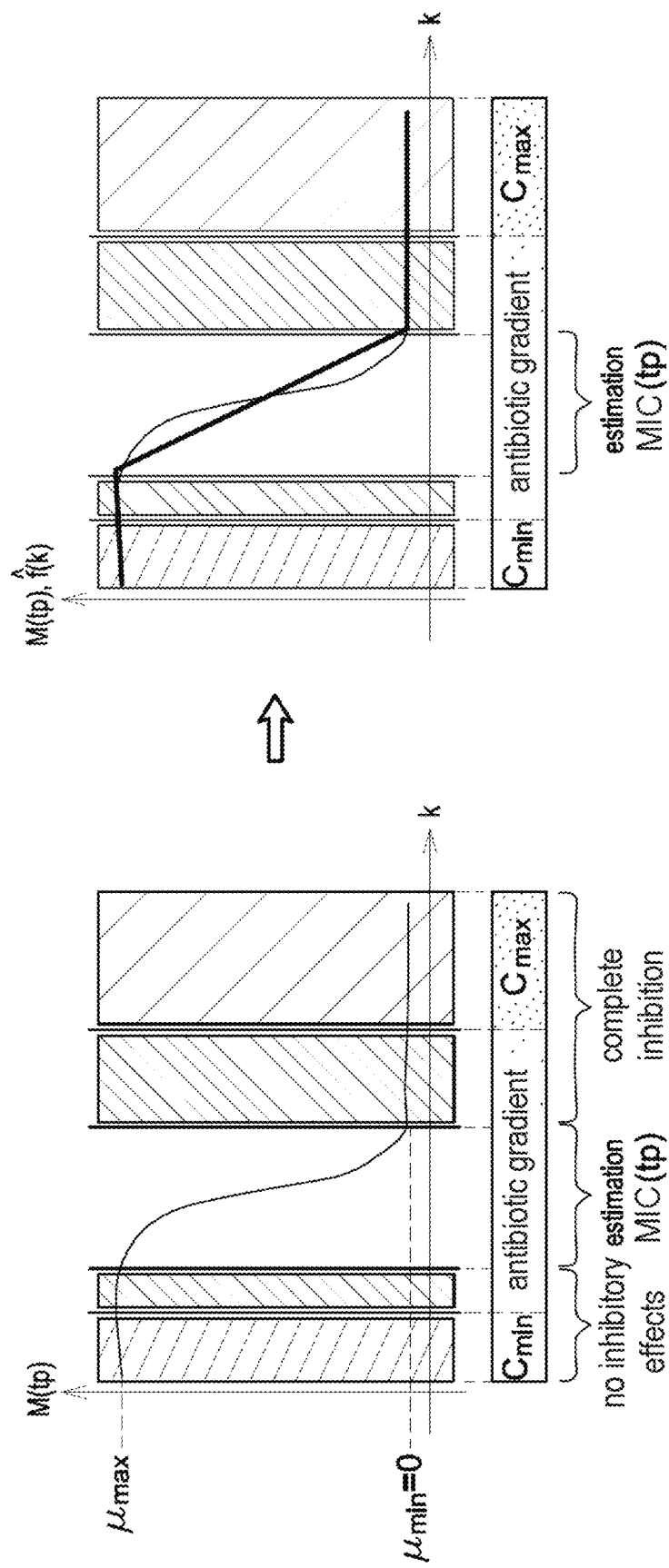
FIGS. 16A and 16B are diagrams illustrating respectively a transition phase in a sequence of maximum growth rates and the approximation of the sequence of maximum growth rates by a piecewise linear function.

A sequence $M(t_P)$ and a sequence $\Lambda(t_P)$ are illustrated in FIGS. 14 and 15 respectively, as a function of the number k of the droplets, for a time point $t_P$ equal to 6 hours.

The processing 52 continues, at 68, with determination of a true minimum inhibitory concentration $MIC(t_P)$ for the time point $t_P$ as a function of at least one of the sequences of parameters determined, for example the sequence $M(t_P)$. This determination is based on searching for a transition zone in the sequence of parameters comprising the concentration $MIC(t_P)$. This zone is defined as the range of initial concentrations of antibiotic of minimum width for which the antibiotic has an observable inhibitory effect on the growth of the bacteria. Referring to FIG. 16A, which illustrates the sequence $M(t_P)$ of FIG. 14 as a function of the number k of the droplets, it is observed that the curve $M(t_P)$ is roughly constant and equal to $\mu_{max}$ over a range $[1; N_0]$ with $N_0 > N_g^{min}$. Similarly, the curve $M(t_P)$ is roughly zero over a range $[N_{MIC(t_P)}; N]$ with $N_{MIC(t_P)} < N_g^{max}$ of the droplets with initial concentration of antibiotic $C_{max}$. The range $[N_0; N_{MIC(t_P)}]$ therefore corresponds to the transition zone, the upper limit of this range corresponding to the required concentration $N_{MIC(t_P)}$.

Identification of the transition zone $[N_0; N_{CMI(t_P)}]$ in step 66 may be performed by any known mathematical method, notably any method for identifying inflexion points on a curve, and therefore for identifying two inflexion points flanking the transition zone.

For example, the curve $M(t_P)$ is approximated by a piecewise linear continuous function $\hat{f}(k)$ according to the relation:

$$\hat{f}(k) = \begin{cases} a \cdot k + b & \forall k \in [1; N_0[ \\ a \cdot k + \beta & \forall k \in [N_0; N_{MIC(t_P)}] \\ c \cdot k + d & \forall k \in ]N_{MIC(t_P)}; n] \end{cases}$$

where the values of the parameters $N_0$, $\alpha$, $\beta$, a, b, c, d, and $N_{MIC(t_P)}$ are calculated in a manner known per se as the optimal solution of an optimization problem minimizing an estimation error between the sequence $M(t_P)$ and the sequence $\{\hat{f}(1), \hat{f}(2), \ldots, \hat{f}(k), \ldots, \hat{f}(N)\}$.

Other approximations of the sequence $M(t_P)$ are possible, for example a polynomial approximation, notably obtained by the method of splines.

Step 64 then continues, at 70, with the determination, and storage, of the initial concentration of antibiotic corresponding to the droplet number $N_{MIC(t_P)}$ according to the relation:

$$MIC(t_P) = [\widehat{ATB}]_{ini(N_{MIC(t_P)})}$$

In a next step 72, a stability test of the concentration $MIC(t_P)$ is performed. The test consists for example of verifying whether the sequence formed from the concentrations $MIC(t_P)$ calculated for T last fluorescence measurement cycles, for example the last 3 cycles, is stable. The concentration is deemed stable for example when it varies by less than S %, for example 5%, for the last T measurement time points. The stability test notably makes it possible to stop the process at the earliest moment so that it is not necessary to select a minimum incubation time a priori.

Figure 17:
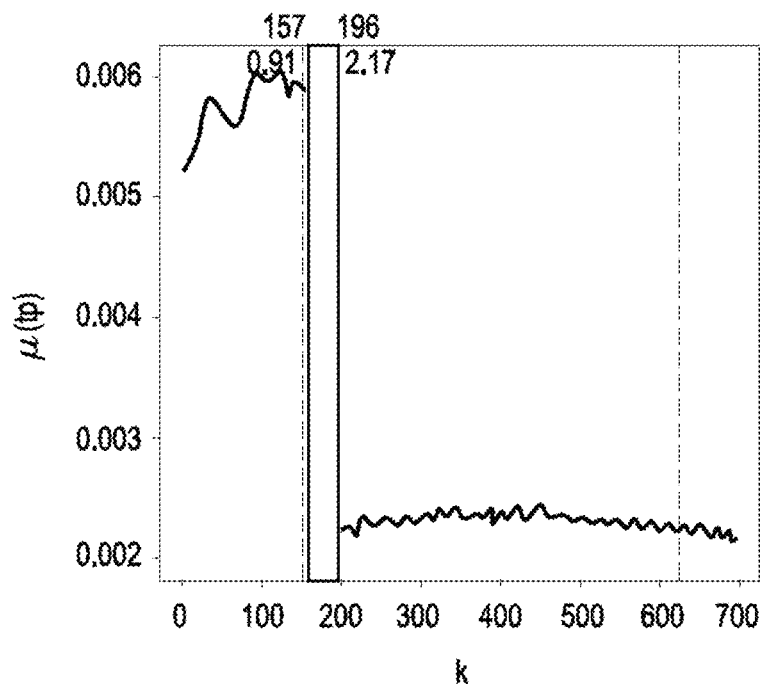
FIGS. 17 and 18 are diagrams illustrating transition zones obtained respectively on a sequence of maximum growth rates and a sequence of lag phase times.
Figure 18:
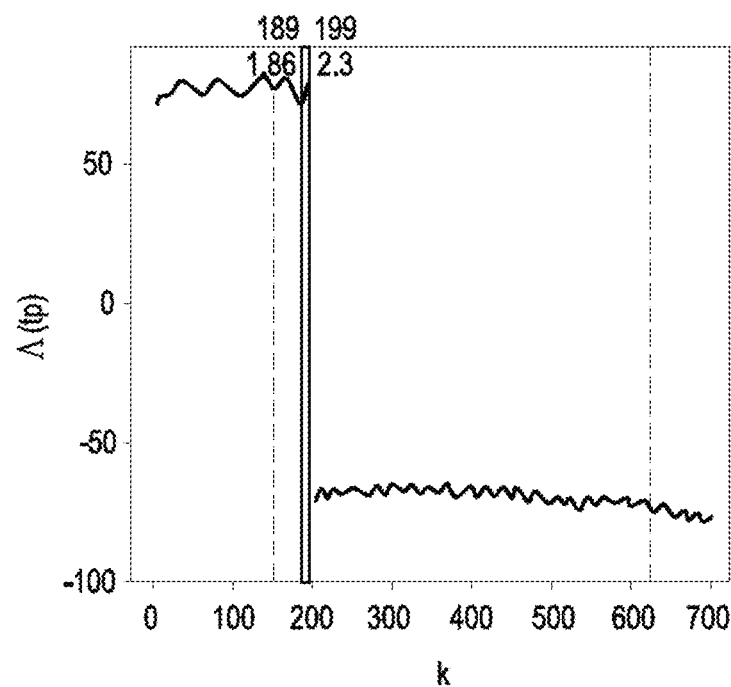

FIGS. 17 and 18 illustrate calculation of the range $[N_0; N_{MIC(t_P)}]$ respectively for the sequences $M(t_P)$ and $\Lambda(t_P)$ in FIGS. 14 and 15. The range $[N_0; N_{MIC(t_P)}]$ determined for the sequence $M(t_P)$ is equal to [157; 196], which corresponds to the concentration range [0.97; 2.17]. The range $[N_0; N_{MIC(t_P)}]$ determined for the sequence $\Lambda(t_P)$ is equal to [189; 199], which corresponds to the concentration range [0.97; 2.3]. Note that the numbers $N_{MIC(t_P)}$ determined for the two parameters are very close (196 and 199 respectively). For its part, the range $[N_0; N_{MIC(t_P)}]$ is determined with greater precision by means of the sequence $\Lambda(t_P)$, whose transition zone is more abrupt than the transition zone of the sequence $M(t_P)$.

If the concentration $MIC(t_P)$ is not stable, step 72 loops back to step 66 for calculating a concentration $MIC(t_P)$ as a function of the new fluorescence measurements. In contrast, if the concentration $MIC(t_P)$ is stable, stopping of the measurements is then commanded at 74. The last concentration $MIC(t_P)$ calculated and stored is then the minimum inhibitory concentration of the antibiotic for the bacterium that is the object of the measurements.

Figure 6A:
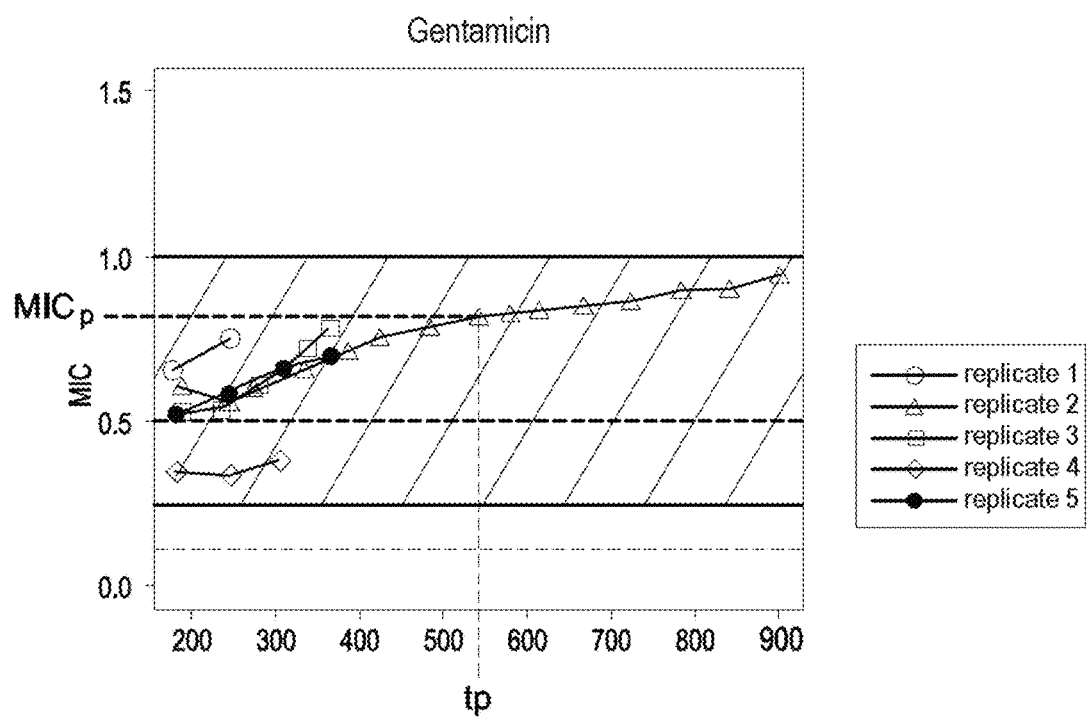
FIGS. 6A to 6C are diagrams illustrating determination of the minimum inhibitory concentration by a cutting method of the prior art, for tests performed on *E. coli* with three different antibiotics.
Figure 6B:
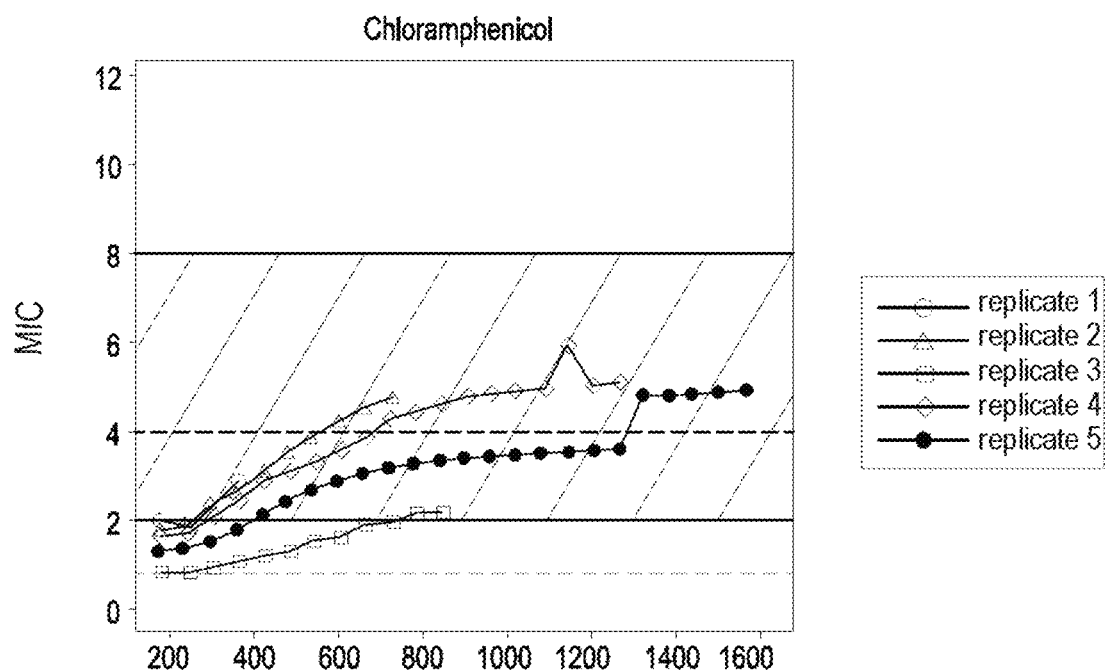
Figure 6C:
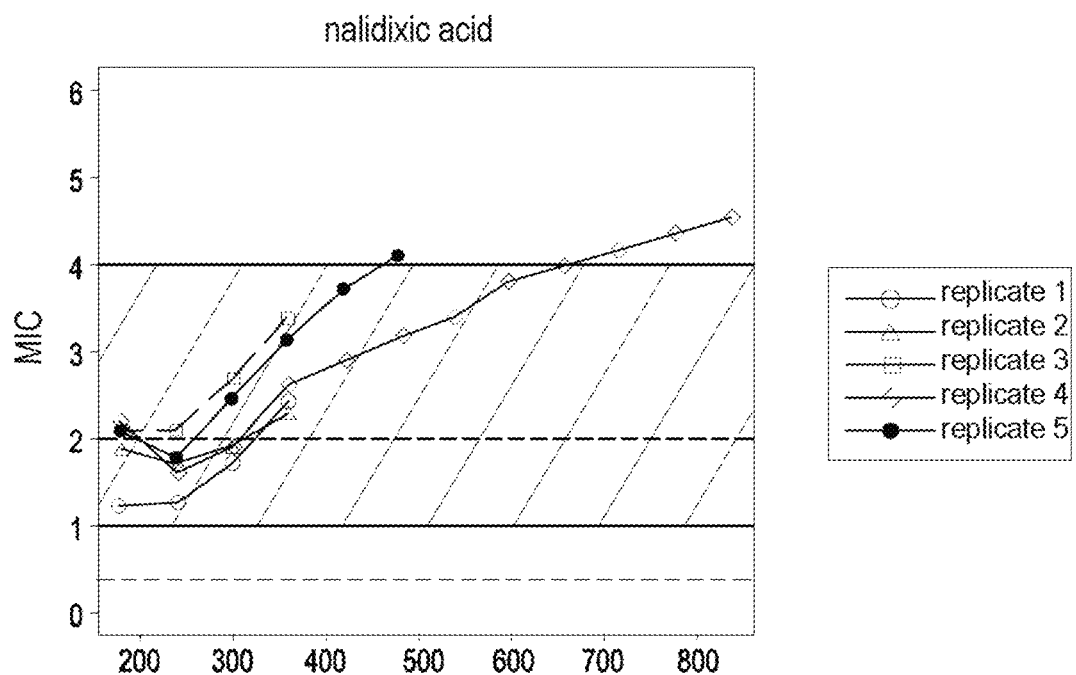
Figure 19A:
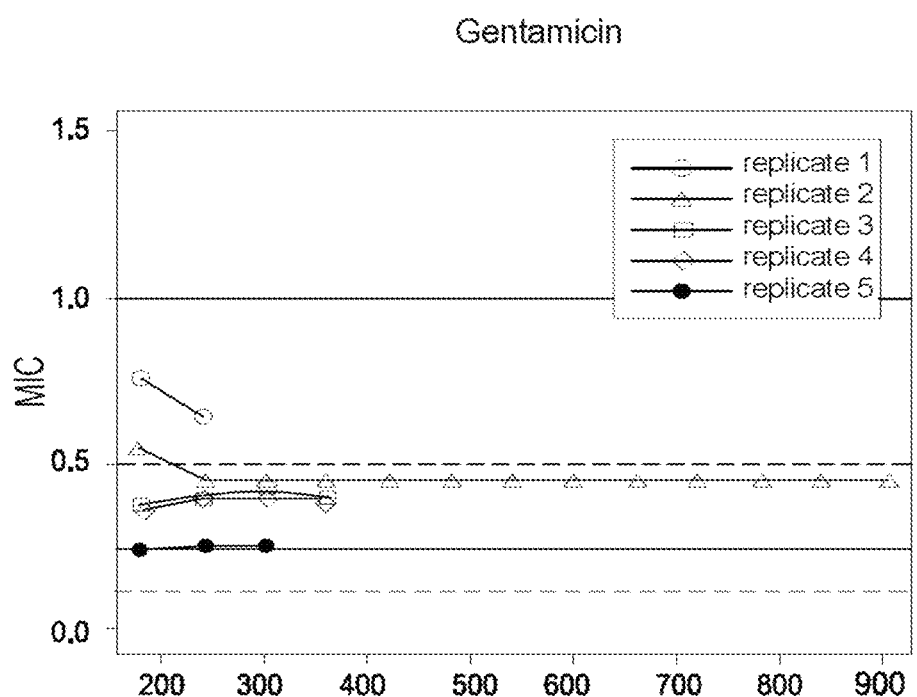
FIGS. 19A to 19C are diagrams illustrating determination of the minimum inhibitory concentration according to the invention, for the tests performed on E. coli with three different antibiotics in FIGS. 6A to 6C.
Figure 19B:
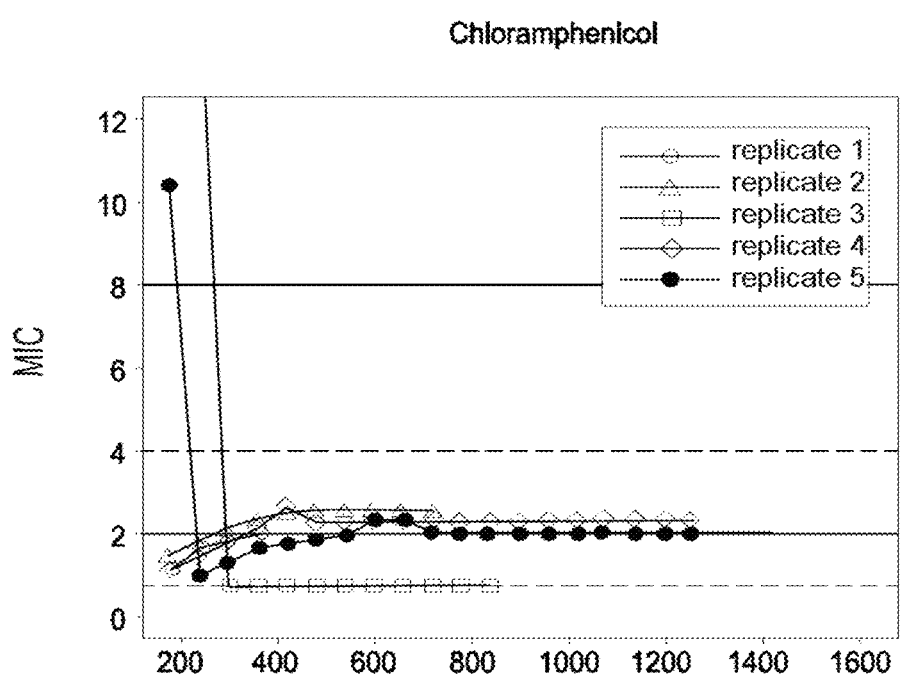
Figure 19C:
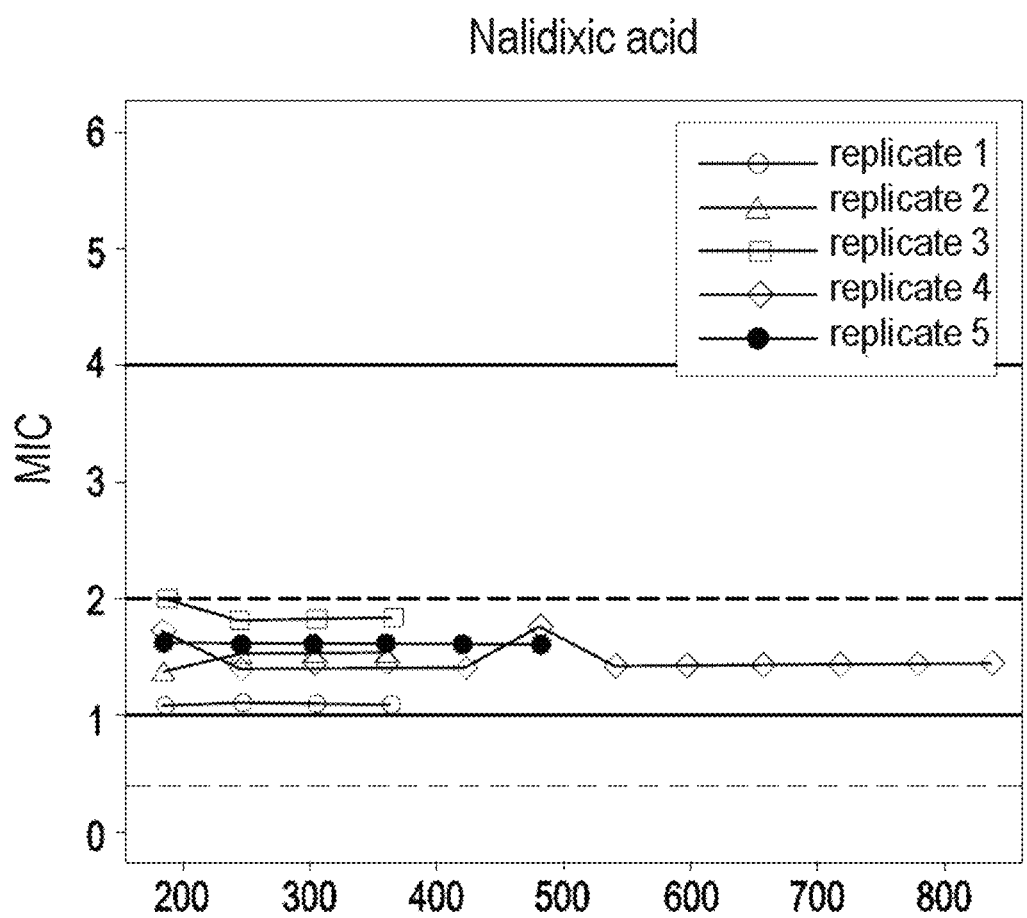

FIGS. 19A to 19C illustrate the results of the embodiment just described. Production of the measurements is that described in relation to FIGS. 6A to 6C. More particularly, the measurements described in these figures form the object of data processing in the processing step 52 described above using the sequence $M(t_P)$ for calculating the concentration $MIC(t_P)$. As can be seen, the concentration $MIC(t_P)$ quickly reaches a stable value that is within the tolerance range of the regulatory MIC. Concerning replicate 3 in FIG. 19B, the particular form of $MIC(t_P)$ results from a calibration error of the droplet production system detected a posteriori.

Variants

A particular embodiment of the invention has been described. Obviously the invention is not limited to this embodiment. Notably the following variants, alone or in combination, form part of the invention.

The embodiment is described for application to estimation of a minimum concentration of antibiotic inhibiting the growth of bacteria and a range of inhibitory concentrations. The invention also applies to determination of other quantities that are characteristic of the inhibitory capacity of the antibiotic.

A particular embodiment has been described, applied to analysis of the inhibitory capacity of an antibiotic on bacterial growth. The invention applies in the same way to analysis of the inhibitory capacity of any molecule on a microorganism, notably analysis of the inhibitory effect of an antifungal on a mold, fungus or yeast.

A particular embodiment has been described in which a single type of antibiotic is present in the samples. As a variant, the samples may comprise a second antibiotic of known concentration. Investigation of the synergies of the antibiotics may thus be undertaken. For example, the method according to the invention is carried out for different concentrations of the second antibiotic.

An embodiment has been described in which the bacteria are initially in large number to avoid exacerbating particular features. As a variant, a smaller bacterial count, or even a single bacterium, is present in the samples in order to study the latter in particular.

An embodiment has been described in which a gradient of initial concentration of antibiotic is produced. As a variant, the concentration of the antibiotic is constant and a bacterial concentration gradient is produced. In general, the invention thus relates to the formation of a gradient of an initial amount of a molecule per microorganism, between a minimum amount $Q_{min}$ and a maximum amount $Q_{max}$.

A gradient has been described that increases linearly from an initial value to a final value. A linear gradient allows each concentration zone to be considered with equal importance. Other types of gradient, notably nonlinear, are of course possible. For example, plateau gradients, where a large number of droplets, for example some tens to about a hundred, are generated for a limited number of concentration values, for example about ten, distributed over the concentration range $[C_{min}; C_{max}]$ of the antibiotic in question. Advantageously, these concentration values are selected as a function of the recommendations of the regulatory authorities relating to application of the reference method by microdilution such as the CA-SFM (Antibiogram Committee of the French Society of Microbiology) or EUCAST (European Committee on Antimicrobial Susceptibility Testing), so as to perform multiple repetitions (some tens to about a hundred, depending on the number of drops per plateau) of a microdilution experiment, in a single experiment.

Processing of fluorescence measurements $x^k$ has been described. Of course, the invention also applies to processing carried out on any value deduced bijectively from the measurements $x^k$, for example the number of bacteria, which is calculated as a function of $x^k$ in a manner known per se.

Calculation of parameters of a growth model has been described, for taking into account the history of growth of the bacteria in the determination of a quantity, for example the MIC.

As a variant, the history is taken into account by calculating a variation $V^k$ of the measurement $x^k$ as a function of time. For example, this variation $V^k(t_P)$ is equal to $(x^k(t_P^k) - x^k(t_{P-1}^k))$, or equal to the mean $$\frac{1}{P} \sum_p (x^k(t_p^k) - x^k(t_{p-1}^k)),$$

or equal to $\max_p(x^k(t_p^k) - x^k(t_{p-1}^k))$. Calculation of $MIC(t_P)$ as a function of $V^k(t_P)$ is performed identically or similarly to that described in relation to the values $\mu_k(t_P)$ and $\lambda_k(t_P)$.

Moreover, determination of the quantity as a function of a parameter ($\mu^k(t_P)$ or $\lambda^k(t_P)$) has been described. As a variant, a quantity, for example the MIC, may be calculated for each parameter of a set of parameters and the final MIC is calculated as a function of, or is selected from, the calculated MIC values. For example, the final MIC is equal to the mean value of the MICs.

An embodiment has been described in which the MIC is equal to the last value calculated that is deemed stable. As a variant, the method continues for several cycles once the MIC has converged and the final MIC is calculated as the average of the values of MIC calculated once convergence was obtained.

An embodiment has been described using the analyzer described in the article "*Millifluidic droplet analyser for microbiology*". Of course, the invention applies to any type of device and method producing a plurality of samples having a gradient of inhibitor and/or a gradient of a microorganism sensitive to said inhibitor. Notably, the invention applies for example to samples that do not have the same volume.

Determination of an MIC has been described, namely the MIC that is deemed to be true, the latter being equal to the upper limit of the range $[N_0; N_{CMI(t_P)}]$. Of course, the regulatory MIC, for example that fixed by the French government or the US government, may also or alternatively be estimated from this range. In fact, as determination of the range is stable, it is possible to determine a correspondence table, or any other suitable conversion rule, between this range and the regulatory MIC. As an example, it is possible to determine whether the microorganism is sensitive, intermediate or resistant to the molecule according to a regulatory classification comparing an MIC at the critical concentrations of the molecule tolerable by humans. A regulatory classification of this type is for example established by the CA-SFM (Antibiogram Committee of the French Society of Microbiology) or EUCAST (European Committee on Antimicrobial Susceptibility Testing).

The invention claimed is:

1. A method for determining a quantity $G_{inhib}$, comprising:
   preparing a plurality of samples comprising microorganisms, a nutrient medium for the microorganisms, and an amount of an inhibitory molecule per microorganism that increases in a range $[Q_{min},Q_{max}]$ as a function of a predetermined classification of the samples;
   incubating the plurality of samples for a time period;
   measuring growth of the microorganisms in each of the plurality of samples at different incubation times within the time period to obtain growth measurements for each of the plurality of samples; and
   determining the quantity $G_{inhib}$ based on the growth measurements, wherein:
   (i) the microorganisms are of a predetermined type;
   (ii) $Q_{min}$ as a lower limit of the range $[Q_{min},Q_{max}]$ results in no inhibition of the growth of the microorganisms in the plurality of the samples;
   (iii) $Q_{min}$ to $Q_{max}$ of the range $[Q_{min},Q_{max}]$ strictly increases;
   (iv) $Q_{max}$ as an upper limit of the range $[Q_{min},Q_{max}]$ results in complete inhibition of the growth of the microorganisms in the plurality of the samples;
   (v) the quantity $G_{inhib}$ represents a capacity of the inhibitory molecule to inhibit the growth of the microorganisms;
   (vi) determination of the quantity $G_{inhib}$ comprises:
       calculating a plurality of growth values for the microorganisms based on the growth measurements;
       correlating the plurality of growth values with the predetermined classification of the plurality of samples to obtain classified growth values; and
       determining the quantity $G_{inhib}$ as a function of variation found within the classified growth values;
   (vii) the quantity $G_{inhib}$ comprises a range $[Q_{min}^{MIC}, Q_{max}^{MIC}]$ for which the growth of the microorganisms in the plurality of samples is at least partially inhibited; and
   (viii) determination of $[Q_{min}^{MIC}, Q_{max}^{MIC}]$ comprises identifying a transition zone in the variation of the classified growth values and identifying corresponding samples from the plurality of samples that are within the transition zone.

2. The method of claim 1, wherein each growth value is an estimate of a maximum slope $\mu$ in a logarithmic growth phase and/or an estimate of a duration of a lag phase $\lambda$.

3. The method of claim 1, wherein identification of the transition zone comprises determining two inflexion points of the variation found within the classified growth values.

4. The method of claim 1, wherein identification of the transition zone comprises modeling the variation found within the classified growth values by a piecewise linear continuous function comprising two endmost straight-line segments and an intermediate straight-line segment that is the transition zone between the two endmost straight-line segments.

5. The method of claim 1, wherein the quantity $G_{inhib}$ comprises an initial minimum inhibitory amount $Q_{MIC}$ of the inhibitory molecule that completely inhibits the growth of the microorganisms, and the initial minimum inhibitory amount $Q_{MIC}$ is equal to an upper limit $Q_{max}^{MIC}$ of the range $[Q_{min}^{MIC}, Q_{max}^{MIC}]$.

6. The method of claim 1, wherein the lower limit $Q_{min}$ of the range $[Q_{min},Q_{max}]$ is a zero amount of the inhibitory molecule.

7. The method of claim 1, wherein:
   the growth of the microorganisms in each of the plurality of samples is measured at increasing incubation times within the time period to obtain the growth measurements for each of the plurality of samples;
   a plurality of quantities $G_{inhib}$ are determined over time based on the growth measurements as a function of the increasing incubation times;
   the plurality of the quantities $G_{inhib}$ are analysed to determine when the quantities $G_{inhib}$ stabilize over time to identify a stabilized quantity $G_{inhib}$;
   the stabilized quantity $G_{inhib}$ represents the capacity of the inhibitory molecule to inhibit the growth of the microorganisms; and
   the stabilized quantity $G_{inhib}$ comprises the range $[Q_{min}^{MIC}, Q_{max}^{MIC}]$ for which the growth of the microorganisms in the plurality of samples is at least partially inhibited.

8. The method of claim 1, wherein the plurality of samples each comprise at least 100 microorganisms.

9. The method of claim 1, wherein the plurality of samples each comprise at least 500 microorganisms.

10. The method of claim 1, wherein the plurality of samples comprise an amount of another inhibitory molecule per microorganism.

11. The method of claim 1, wherein the microorganisms are at a constant concentration among the plurality of samples.

12. The method of claim 1, wherein the microorganisms are a type of bacteria and the inhibitory molecule is an antibiotic.

13. The method of claim 1, wherein the microorganisms are a type of yeast or mold and the inhibitory molecule is an antifungal.

14. The method of claim 1, wherein the nutrient medium comprises an element that is metabolized by the microorganisms to form fluorescent molecules during the growth of the microorganisms and the growth of the microorganisms is measured by measuring fluorescence from the fluorescent molecules.

15. The method of claim 1, wherein absorbance among the plurality of samples is variable as a function of quantity of the microorganisms and the growth of the microorganisms is measured by measuring optical density.

16. The method of claim 1, wherein preparation of the plurality of samples comprises producing a train of droplets as the plurality of samples in oil.

17. A device for determining a quantity $G_{inhib}$, comprising:
   means for preparing a plurality of samples comprising microorganisms, a nutrient medium for the microorganisms, and an amount of an inhibitory molecule per microorganism that increases in a range $[Q_{min},Q_{max}]$ as a function of a predetermined classification of the samples;

means for incubating the plurality of samples for a time period;

means for measuring growth of the microorganisms in each of the plurality of samples at different incubation times within the time period to obtain growth measurements for each of the plurality of samples; and means for determining the quantity $G_{inhib}$ based on the growth measurements, wherein:

(i) the microorganisms are of a predetermined type;

(ii) $Q_{min}$ as a lower limit of the range $[Q_{min}, Q_{max}]$ results in no inhibition of the growth of the microorganisms in the plurality of the samples;

(iii) $Q_{min}$ to $Q_{max}$ of the range $[Q_{min}, Q_{max}]$ strictly increases;

(iv) $Q_{max}$ as an upper limit of the range $[Q_{min}, Q_{max}]$ results in complete inhibition of the growth of the microorganisms in the plurality of the samples;

(v) the quantity $G_{inhib}$ represents a capacity of the inhibitory molecule to inhibit the growth of the microorganisms;

(vi) determination of the quantity $G_{inhib}$ comprises:

calculating a plurality of growth values for the microorganisms based on the growth measurements;

correlating the plurality of growth values with the predetermined classification of the plurality of samples to obtain classified growth values; and determining the quantity $G_{inhib}$ as a function of variation found within the classified growth values;

(vii) the quantity $G_{inhib}$ comprises a range $[Q_{min}^{MIC}, Q_{max}^{MIC}]$ for which the growth of the microorganisms in the plurality of samples is at least partially inhibited; and (viii) determination of $[Q_{min}^{MIC}, Q_{max}^{MIC}]$ comprises identifying a transition zone in the variation of the classified growth values and identifying corresponding samples from the plurality of samples that are within the transition zone.

18. The device of claim 17, wherein each growth value is an estimate of a maximum slope $\mu$ in a logarithmic growth phase and/or an estimate of a duration of a lag phase $\lambda$.

19. The device of claim 17, wherein identification of the transition zone comprises determining two inflexion points of the variation found within the classified growth values.

20. The device of claim 17, wherein identification of the transition zone comprises modeling the variation found within the classified growth values by a piecewise linear continuous function comprising two endmost straight-line segments and an intermediate straight-line segment that is the transition zone between the two endmost straight-line segments.

* * * * *